United States Patent [19]

Utas

[11] Patent Number: 5,853,518
[45] Date of Patent: Dec. 29, 1998

[54] CATHETER

[75] Inventor: Jan Utas, Kungsbacka, Sweden

[73] Assignee: Astra Aktiebolag, Sodertalje, Sweden

[21] Appl. No.: 586,762

[22] PCT Filed: Dec. 20, 1995

[86] PCT No.: PCT/SE95/01558

§ 371 Date: Jan. 30, 1996

§ 102(e) Date: Jan. 30, 1996

[87] PCT Pub. No.: WO96/19254

PCT Pub. Date: Jun. 27, 1996

[30] Foreign Application Priority Data

Dec. 22, 1994 [SE] Sweden ................................ 9404486

[51] Int. Cl.⁶ .................................................. A61M 25/16
[52] U.S. Cl. ...................... 156/245; 156/278; 156/304.2; 427/2.3; 604/265; 604/280
[58] Field of Search .................................. 156/245, 278, 156/304.2; 427/2.11, 2.12, 2.28, 2.3; 604/264, 265, 280, 282

[56] References Cited

U.S. PATENT DOCUMENTS

| 3,566,874 | 3/1971 | Shepherd | 604/265 |
|---|---|---|---|
| 4,188,954 | 2/1980 | Patel et al. . | |
| 4,585,666 | 4/1986 | Lambert | 604/280 |
| 4,666,437 | 5/1987 | Lambert | 604/265 |
| 4,773,901 | 9/1988 | Norton | 604/265 |
| 4,863,442 | 9/1989 | DeMello | 604/282 |
| 4,898,591 | 2/1990 | Jang | 604/282 |
| 4,906,237 | 3/1990 | Johansson et al. | 604/265 |
| 5,217,493 | 6/1993 | Raad | 604/265 |

FOREIGN PATENT DOCUMENTS

| 0336984 | 10/1989 | European Pat. Off. . |
|---|---|---|
| 398048 | 12/1977 | Sweden . |
| 1436679 | 5/1976 | United Kingdom . |
| 2075347 | 11/1981 | United Kingdom . |
| 2156680 | 10/1985 | United Kingdom . |
| 8902763 | 4/1989 | WIPO . |
| 9207607 | 5/1992 | WIPO . |

*Primary Examiner*—Daniel Stemmer
*Attorney, Agent, or Firm*—White & Case L.L.P.

[57] ABSTRACT

A process for manufacturing a catheter for insertion into a body cavity, for instance a catheter used for insertion into the urethra. The catheter has a tip portion provided with one or several drainage or flushing openings adjacent to the free end which is to be inserted into the body cavity. The outside of the catheter is provided with a coating. The process includes injection-molding a separate tip portion of the catheter. The tip portion includes an inner lumen and the drainage/flushing openings. The inner and outer diameters of the tip correspond to those of a standard tube. An end of a standard tube and an end of the tip portion are formed to conform to each other. These formed ends are then joined in a joining operation. The coating is applied to the standard tube before the joining operation is performed.

12 Claims, No Drawings

CATHETER

TECHNICAL FIELD OF THE INVENTION

The present invention relates to a process for manufacturing a catheter, for instance of the type used for insertion into the urethra, said catheter preferably being coated by a layer of a hydrophilic material, said catheter further being provided with a drainage or flushing opening adjacent to the free end which is to be inserted into the urethra.

BACKGROUND TO THE INVENTION

Hydrophilic coated catheters are known, for example, from U.S. Pat. No. 4,585,666 and U.S. Pat. No. 4,666,437 (Lambert/Astra Meditec AB) or U.S. Pat. No. 4,906,237 (Johansson et al./Astra Meditec AB).

U.S. Pat. No. 4,773,901 (Norton/C. R. Bard, Inc.) discloses a catheter with a selectively rigidified tip portion. The tip is coated with a hydrophilic polymer which absorbs or adsorbs water in use so as to render the tip soft.

A commonly used technique when manufacturing catheters of the above kind is to use an extruded flexible tube made of polymer material such as PVC or polyethylene or a similar material and which has appropriate dimensions as a starting material. The end of the tube is welded or melted shut or otherwise closed at one end. If so desired, the outside of the catheter is then provided with a hydrophilic layer. The drainage/flushing hole is then punched into the tube.

A first way of performing the punching operation may be by means of a glancing movement relative to the tube in which a part-circular part of the sidewalls of the tube is cut away by means of the punch. A disadvantage with this punching operation is the difficulty to obtain an exact size of the hole, since a small error in the alignment of the punch or in the tubing dimension will result in a great difference in the size of the punched hole. This difficulty in obtaining an exact size of the hole may be remedied by using a second way of performing the punching operation. In this second operation the punch is centred over the tube and lowered on to the tube, compressing the sidewalls of the tube onto each other and punching through the uppermost sidewall, and stopping the punching operation well before there is any risk of penetrating the lower sidewall. The hole resulting from this punching operation will always be of the same size. The difficulties connected with this operation is to decide exactly when to stop the punch so as to be sure that one sidewall has been fully penetrated but the other sidewall with certainty has not been penetrated. It may be easier to adjust the punch exactly when holes are punched in uncoated standard tubes having well-defined wall thicknesses, but it may be different when the tube has been coated with a layer, for instance a hydrophilic layer, since the layer affects the dimensions of the tubing, at least to some extent.

Another problem in the manufacture of coated catheters arises when a catheter made from a standard tube is formed with a curved tip (for instance a so called Tiemann-catheter), since the heat treatment connected with the coating procedure or with a subsequent sterilisation may result in that the tip straightens again due to the "memory" of or to the remaining, unrelieved tensions in the polymer in the tube. The "memory" of the material may be defined as the tendency of the material to resume its original shape due to the inherent orientation of the material.

DISCLOSURE OF THE INVENTION

In accordance with the invention the above difficulties are resolved in that the tip portion of the catheter, including an inner lumen and a drainage/flushing hole is injection moulded with inner and outer diameters corresponding to those of a standard tube and subsequently joined to said standard tube.

Thus, according to the present invention there is provided a process for manufacturing a catheter for insertion into a body cavity, for instance of the type used for insertion into the urethra, said catheter having a tip portion provided with one or several drainage or flushing openings adjacent to the free end which is to be inserted into said body cavity, the outside of the catheter being provided with a coating, characterized in that said process comprises the steps of:

injection-moulding a separate tip portion of the catheter, said tip portion including an inner lumen and said drainage/flushing openings, the inner and outer diameters of said tip corresponding to those of a standard tube, forming an end of a standard tube and an end of said tip portion to conform to each other for a subsequent joining operation, and joining said tip to said standard tube in said joining operation, wherein the coating is applied to the standard tube before the joining operation is performed.

Difficulties encountered with punching coated tubes are thus eliminated.

Such a process furthermore allows the coating to extend over the entire length of the catheter, including the edges of the drainage/flushing openings. This may be achieved by coating the tip after the joining operation is performed. This way, it is not necessary to immerse the entire assembled catheter into the coating medium.

Coating would normally be achieved by mounting the catheter on rods or pins of stainless steel. If the entire assembled catheter were immersed into the coating medium, the rods would become contaminated with the solution, as it can enter through the opening in the tip. Use of the present invention means that, after the joining operation is performed, the catheter need only be immersed as far as the region of the join. Internal coating of the catheter is also thus minimized.

In fact, we prefer also to provide the injection-moulded tip with a coating before the joining operation is performed. This way, no substantial coating step need be performed after the joining operation is performed.

On the other hand, if, after the joining operation is performed, a second coating operation is performed, we ensure that the area of the catheter in the region of the join is coated. It may be difficult to get the second coating to stick, though this can be achieved by scratching some of the existing coating off, say 2 mm, before the second coating operation is performed.

Before the joining operation is performed, the coating may be applied to the standard tube by the further steps of:

fusing or otherwise plugging one end of said standard tube, coating the outside of the catheter with a layer, and cutting off the fused end or otherwise unplugging said end.

This way, possible coating of the stainless steel rods and interior of the catheter during this stage of the manufacture is completely eliminated.

Any method may be used for joining the tip to the standard tube, such as snapping together or even screwing. However, we prefer for the tip to be welded, glued or solvent-glued to the standard tube. Glue compatible with the solvent used for coating could be used, e.g. a glue which dissolves in the solvent, so as to assist adhesion. The glue may extend partly into the lumen, but must not go too far, as this would reduce the diameter of the lumen.

Using an oblique cut could cause problems with orientation of the standard tube relative to the tip. Thus preferably a straight cut perpendicular to the axis of the standard tube is used.

Any type of coating may be used, but the invention is particulary suitable if the coating is a hydrophilic coating.

The invention allows a great deal of versatility in the type of tips that may be used. Thus, the tip may be moulded to a curved shape, as in a Tiemann catheter. The invention gives a more stable shape to these.

Similarly, the tip does not need to be of the same material of the standard tube. It may be moulded from a material which is softer than the material in the standard tube, or which is more rigid than the material in the standard tube. A stiff tip would be used if, for example, prostate problems are manifest.

The tip and standard tube could just as easily be made of the same material. This would make gluing easier.

Preferably the catheter is made of a thermoplastic polymer such as PVC or polyethylene or a similar material. Such materials are ideal if the catheter is an intermittent urinary drainage catheter, as opposed to a balloon catheter for long-term use. There is no need to shrink the tip on to the standard tube, as might be done with balloon catheters.

In a further aspect of the invention, there is provided a catheter made by such a process.

DETAILED DESCRIPTION OF A PREFERRED EMBODIMENT OF THE INVENTION

A preferred embodiment of the invention will now be described, by way of example. In the preferred embodiment, the catheter is coated with a hydrophilic layer, for instance in accordance with U.S. Pat. Nos. 4,585,666 and 4,666,437 (Lambert/Astra Meditec AB) or 4,906,237 (Johansson et al./Astra Meditec AB). The catheter is made by joining two parts, namely a part formed by a standard, commercially available tube for instance made of PVC, and a part formed by an injection-moulded tip. Before the joining operation, the two parts of the catheter are coated with a hydrophilic layer.

The two parts of the catheter are coated by immersion in a coating solution. In order to prevent the coating material or coating solution to enter the interior of the tube, the end of the standard tube may be fused or otherwise plugged. The tube of course also may be coated by immersing the entire length of the tube in the coating solution whilst ensuring that the open ends of the tube will not be immersed in the solution. The end of the tube is then cut in order to form an end surface which is suitable for the joining operation which is to be used.

The hollow tip portions for the catheter are made separately by means of injection moulding and the shape and properties of the tip thus can be adapted to the intended use of the catheter. The tip portion is then immersed in the coating solution. In one embodiment the tip portion is held on a mandrel filling or sealing the inner lumen of the tip portion, the tip portion after the immersion being removed from the mandrel, but the coating solution may in some instances also be allowed to reach the inner lumen of the tip. The hindmost (in use) or proximal end of the tip portion is then cut to a shape complementary to the shape of the cut end of the coated tube, and the two parts are joined together. The two parts can be glued together by means of an appropriate glue or be solvent-glued, i.e. the ends of the two catheter parts are slightly dissolved in a suitable solvent and then pressed together. The two parts may also be welded together, for instance ultrasonically.

The invention described above has several important advantages.

The openings in the catheter can be made round with smooth edges and constantly with the same size. The edges of the openings will also be coated. An injection-moulded, curved "Tiemann"-tip will be more inclined to keep the desired shape after the heat treatment which may be involved in a coating and/or sterilizing treatment in comparison to a catheter which has been formed (or, moreover, deformed) to a curved shape. If desired, the tip can be moulded from a material which may be harder or softer than the material in the tube. The shape of the tip can be varied to a large extent so as to obtain a large number of different catheters for different uses. One variation might for instance be a "terminal eye", i.e. a rounded opening at the end of the catheter.

It consequently will be easy to manufacture a wide range of catheters well adapted to different uses and well adapted to different types, shapes and courses of the body cavities into which the catheters are to be inserted as well as to the way the catheters are to be inserted.

The assortment of the catheters will be modularized since the same type of tip will be used for different catheter lengths. Finally, the length of the catheter may be decided after the coating procedure, since the shrinking problem will be of lesser importance than in the catheters presently commercially available. Unrelieved tensions in the polymer material in the tube part of the catheter remaining as a result of the manufacturing procedure may lead to shrinking in subsequent heat treatments such as coating or sterilizing procedures.

I claim:

1. A process for manufacturing a catheter for insertion into a body cavity, said catheter having a tip portion and a tube portion, said tip portion being provided with one or more drainage or flushing openings, said tip portion being at the end of the catheter which is inserted into the body cavity, the outside of the catheter being provided with a coating substantially along the entire length of said catheter, the process comprising the steps of:

forming said tip portion by injection molding, said tip portion being formed separate from the tube portion, said tip portion including an inner lumen and said one or more drainage or flushing openings, the inner and outer diameter of said tip portion corresponding to the inner and outer diameter of said tube portion;

forming an end of the tube portion and an end of the tip portion to conform to each other for a subsequent joining operation; and joining said tip portion to said tube portion;

wherein the coating is applied to said tube portion before the joining operation is performed.

2. A process according to claim 1, characterized in that the injection-molded tip portion is also provided with a coating over substantially the entire outer surface of the tip portion before the joining operation is performed.

3. A process according to any one of claims 1 or 2, characterized in that, after the joining operation is performed, a second coating is applied over at least the area of the catheter in the region where the tip portion is joined to the tube portion.

4. A process according to any one of claims 1 or 2, characterized in that said coating is applied to the tube portion by the further steps of:

fusing or otherwise plugging one end of said tube portion, coating the outside of said tube portion with a layer of said coating, and cutting off the fused end or otherwise unplugging said end before the joining operation is performed.

5. A process according to any one of claims 1 or 2, characterized in that said tip portion is welded, glued or solvent-glued to said tube portion.

6. A process according to any one of claims 1 or 2, characterized in that said coating is a hydrophilic coating.

7. A process according to any one of claims 1 or 2, characterized in that said tip portion is molded to a curved shape.

8. A process according to any one of claims 1 or 2, characterized in that said tip portion is molded from a material which is softer than the material in the tube portion.

9. A process according to any one of claims 1–2, characterized in that said tip portion is molded from a material which is more rigid than the material in the tube portion.

10. A process according to any one of claims 1 or 2, characterized in that said catheter is made of a thermoplastic polymer.

11. A process according to claim 10, characterized in that said thermoplastic polymer comprises PVC or polyethylene or a similar material.

12. A process according to any one of claims 1 or 2, characterized in that said catheter is an intermittent urinary drainage catheter.

* * * * *